(12) United States Patent (10) Patent No.: US 7,102,508 B2
Edelstein et al. (45) Date of Patent: Sep. 5, 2006

(54) METHOD AND APPARATUS FOR LOCATING AND TRACKING PERSONS

(75) Inventors: Peter Seth Edelstein, Menlo Park, CA (US); Benjamin Theodore Nordell, II, San Mateo, CA (US)

(73) Assignee: Persephone, Inc., Menlo Park, CA (US)

( * ) Notice: Subject to any disclaimer, the term of this patent is extended or adjusted under 35 U.S.C. 154(b) by 0 days.

(21) Appl. No.: 10/651,635

(22) Filed: Aug. 29, 2003

(65) Prior Publication Data

US 2004/0174258 A1 Sep. 9, 2004

Related U.S. Application Data

(60) Provisional application No. 60/409,610, filed on Sep. 9, 2002.

(51) Int. Cl.
*G08B 1/08* (2006.01)
(52) U.S. Cl. ............... 340/539.13; 340/573.1; 340/573.3; 342/357.1; 342/450; 600/424; 607/60
(58) Field of Classification Search ............ 340/573.4, 340/573.3, 539.12, 539.13, 825.49; 600/300; 701/214, 218
See application file for complete search history.

(56) References Cited

U.S. PATENT DOCUMENTS

| | | | |
|---|---|---|---|
| 3,866,217 A * | 2/1975 | Bennett, Jr. ............ | 714/715 |
| 4,706,689 A | 11/1987 | Man | |
| 4,952,928 A | 8/1990 | Carroll et al. | |
| 5,010,893 A | 4/1991 | Sholder | |

(Continued)

OTHER PUBLICATIONS

Nolan, T., "The World Today-Researcher defends child tracking microchip", Sep. 4, 2002, ABC Online: http://www.abc.net.au/worldtoday/s677108.htm.

(Continued)

*Primary Examiner*—Benjamin C. Lee
(74) *Attorney, Agent, or Firm*—Michael A. Glenn; Glenn Patent Group

(57) ABSTRACT

The invention relates to a method and apparatus for locating and tracking persons by use of an implantable device. The described invention is an implant able device composed of biocompatible materials in all areas where contact with organic tissue occurs. The gross anatomic siting of the device includes any limb, the torso, including back and perineum, the neck, and the head. The surgical anatomic siting of the device includes: (1) Supramuscular: for example, deep to the epidermis, dermis, and subcutaneous fat, on or attached to muscle and/or muscle fascia. Such a location is currently used for implantation of commercially available buried intravenous access ports, which are positioned on, and attached to, the pectoralis major muscle fascia; (2) Intramuscular: for example, within or between the muscles of a limb; (3) Submuscular: for example, deep to a large muscle. Such a location is currently used for implantation of commercially available artificial urethral and anal sphincter reservoirs, which are positioned deep to the rectus abdominus muscles, within the pre-peritoneal Space of Retzius; (4) Intraluminal: for example, within the lumen of an organ which has a naturally occurring orifice. Such a location is currently used for implantation of commercially available ingested video endoscopy capsule devices, i.e. gastrointestinal tract lumen, and intrauterine contraceptive devices, i.e. uterus lumen; and (5) Intracavitary: for example, intrathoracic or intraperitoneal. Such an intraperitoneal location is currently used for implantation of commercially available intraperitoneal dialysis catheters.

37 Claims, 11 Drawing Sheets

U.S. PATENT DOCUMENTS

| | | | |
|---|---|---|---|
| 5,196,825 A | | 3/1993 | Young |
| 5,218,343 A | | 6/1993 | Strobbe et al. |
| 5,218,344 A | | 6/1993 | Ricketts |
| 5,314,450 A | | 5/1994 | Thompson |
| 5,631,642 A | * | 5/1997 | Brockelsby et al. ........ 340/993 |
| 5,731,757 A | | 3/1998 | Layson |
| 5,936,529 A | | 8/1999 | Reisman |
| 5,940,004 A | | 8/1999 | Fulton |
| 6,121,922 A | * | 9/2000 | Mohan .................... 342/357.1 |
| 6,160,481 A | | 12/2000 | Taylor, Jr. |
| 6,198,390 B1 | | 3/2001 | Schlager et al. |
| 6,198,963 B1 | * | 3/2001 | Haim et al. ................. 600/424 |
| 6,239,700 B1 | | 5/2001 | Hoffman et al. |
| 6,239,705 B1 | | 5/2001 | Glen |
| 6,261,247 B1 | * | 7/2001 | Ishikawa et al. ............ 600/587 |
| 6,297,739 B1 | * | 10/2001 | Small ..................... 340/573.3 |
| 6,317,030 B1 | * | 11/2001 | Magee .................... 340/10.52 |
| 6,334,073 B1 | | 12/2001 | Levine |
| 6,398,710 B1 | | 6/2002 | Ishikawa et al. |
| 6,436,068 B1 | * | 8/2002 | Bardy .......................... 604/57 |
| 6,748,318 B1 | * | 6/2004 | Jones ........................ 701/201 |
| 6,828,908 B1 | * | 12/2004 | Clark .................... 340/539.13 |

OTHER PUBLICATIONS

ANS:Life Gets Bettter; Implantable Therapies for Chronic Pain Mangement and Nuerological Disorders, http://www.ans-medical.com.

Medtronic Sigma™ and Kappa® Pacemakers http://www.medtronic.com.

"Portacaths and Omega Ports" http://www.user.fast.net/~kittenz/Port.html.

* cited by examiner

METHOD AND APPARATUS FOR LOCATING AND TRACKING PERSONS

CROSS-REFERENCE TO RELATED APPLICATIONS

This application claims priority to U.S. Provisional Patent Application Ser. No. 60/409,610 filed Sep. 9, 2002.

BACKGROUND OF THE INVENTION

1. Technical Field

The invention relates to the locating and tracking of persons. More particularly, the invention relates to a method and apparatus for locating and tracking persons by use of an implant able device.

2. Description of the Prior Art

The invention relates to a method and apparatus for locating and tracking persons by use of an implant able device. Other systems with some similar purposes, such as that described in U.S. Pat. No. 5,629,678 (Gargano et al., May 13, 1997) and U.S. Pat. No. 6,317,049 (Toubia et al., Nov. 13, 2001), describe positioning devices which are implanted beneath the skin in subcutaneous location, i.e. beneath the epidermal and dermal layers. There are several significant problems associated with locating a positioning device in the subcutaneous position including, but not limited to:

(1) In cases of abduction, the device is easily located by the abductor. Once located, the position of the device immediately under the skin allows for rapid and relatively simple removal of the device by the abductor without the victim incurring significant medical risk;

(2) In cases of runaway children, the device is easily located by the runaway. Once located, the position of the device immediately under the skin allows for rapid and relatively simple removal of the device without the runaway incurring significant medical risk;

(3) The placement of the device immediately beneath the skin exposes the device to constant and continuous risk of accidental damage and subsequent malfunction as the implanted individual goes through his daily routine. This is especially true for implanted juveniles, who play sports and are physically very active on a daily basis. Any malfunction secondary to accidental damage may not be detected and, therefore, the implanted individual and his loved ones would be unaware that the individual could not be positioned if missing. If damage is detected, surgical removal of the dysfunctional device, plus repeat surgical implantation of a new device, would be required. This exposes the individual to further medical risk and discomfort;

(4) The placement of the device immediately beneath the skin is cosmetically unappealing, as the device appears as a lump under the skin. This aesthetic problem is important in that it may increase resistance against device implantation from the individuals who are most likely to benefit from such implantation, e.g. teenage girls, who are frequent targets of Acquaintance Abduction, according to Office of Juvenile Justice and Delinquency Prevention statistics.

(5) Current Implanted devices relying on a GPS antenna within the device are frequently unable to receive GPS signals due to mechanical signal interference.

It would be advantageous to provide a method and apparatus for locating and tracking persons by use of an implant able device that solved the above identified problems attendant with existing approaches.

SUMMARY OF THE INVENTION

The invention relates to a method and apparatus for locating and tracking persons by use of an implant able device. The described invention is an implant able device composed of biocompatible materials in all areas where contact with organic tissue occurs. The gross anatomic siting of the device includes any limb, the torso, including back and perineum, the neck, and the head. The surgical anatomic siting of the device includes:

(1) Supramuscular: for example, deep to the epidermis, dermis, and subcutaneous fat on or attached to muscle and/or muscle fascia. Such a location is currently used for implantation of commercially available buried intravenous access ports, which are positioned on, and attached to, the pectoralis major muscle fascia;

(2) Intramuscular: for example, within or between the muscles of a limb;

(3) Submuscular: for example, deep to a large muscle. Such a location is currently used for implantation of commercially available artificial urethral and anal sphincter reservoirs, which are positioned deep to the rectus abdominus muscles, within the pre-peritoneal Space of Retzius (also known as the retropubic space);

(4) Intraluminal: for example, within the lumen of an organ which has a naturally occurring orifice. Such a location is currently used for implantation of commercially available ingested video endoscopy capsule devices, i.e. gastrointestinal tract lumen, and intrauterine contraceptive devices, i.e. uterus lumen; and (5) Intracavitary: for example, intrathoracic or intraperitoneal. Such an intraperitoneal location is currently used for implantation of commercially available intraperitoneal dialysis catheters.

DETAILED DESCRIPTION OF THE INVENTION

The presently preferred embodiment of the invention provides a method and an apparatus that serves to locate the position of a human being that is categorized as missing, including juveniles (persons of less than 18 years of age), including (but not limited to) those victims of family abduction, acquaintance abduction, and stranger abduction, as well as runaways (missing person classifications used by the U.S. Office of Juvenile Justice and Delinquency Prevention). Secondary uses of the described invention include locating and positioning of pets, animals, incarcerated individuals, military personnel, business travelers, mentally impaired individuals, and the monitoring of medical functions including (but not limited to) cardiac rate and rhythm, blood pressure, body temperature, and blood oxygen saturation, serum electrolytes, glucose, insulin, etc, as well as the location of objects.

Figure 1:
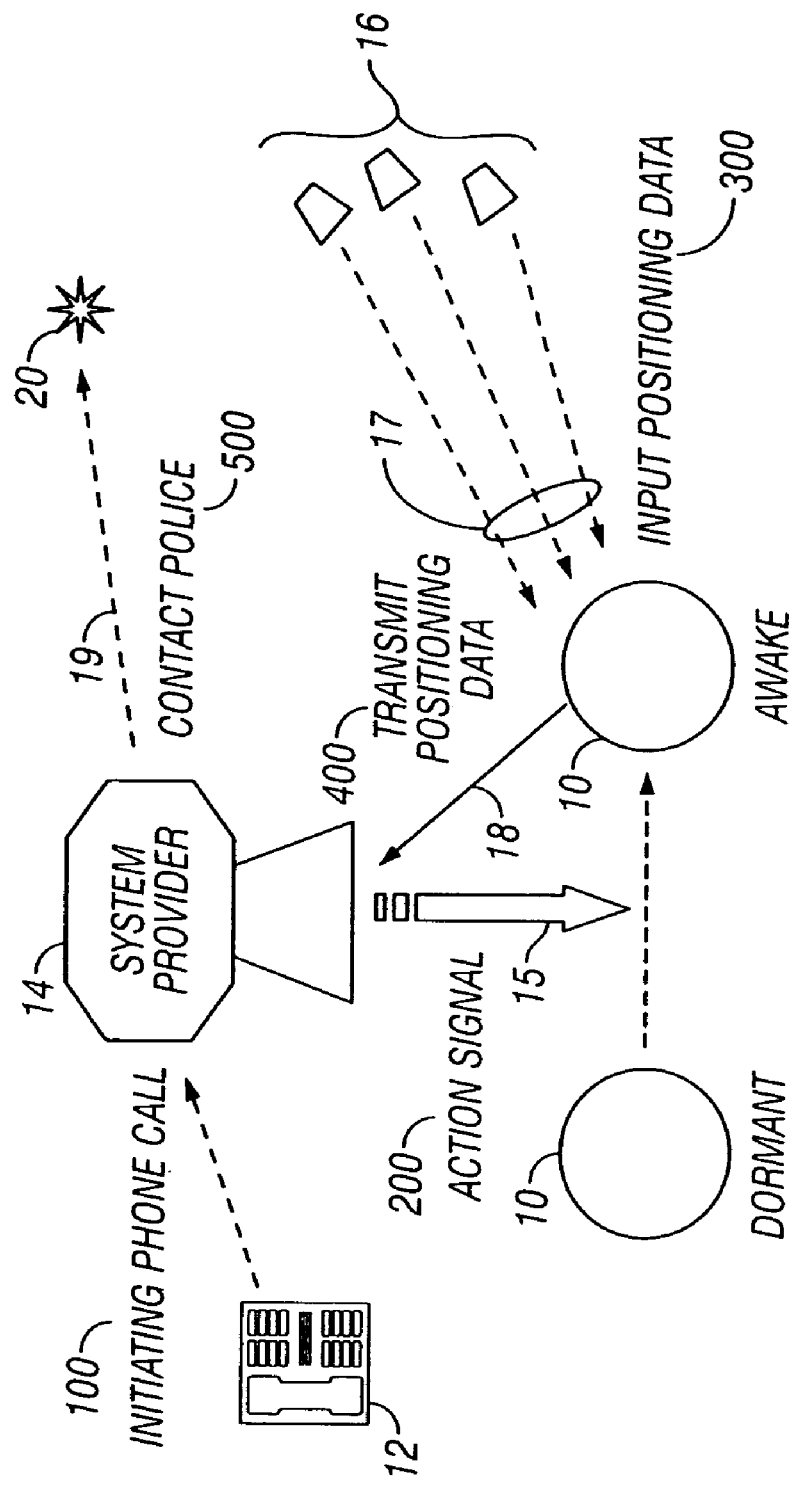
FIG. 1 is a block schematic diagram of a system for locating and tracking persons according to the invention.

FIG. 1 is a block schematic diagram of a system for locating and tracking persons according to the invention. The system comprises a positioning and locating device 10, which is preferably a device that is implanted within an individual in accordance with the various embodiments described below. The preferred embodiment of the invention device reposes in a dormant or semi-dormant, e.g. passive, state within the person. When an activation event occurs (100), such as a telephone call to the device when the person goes missing, a system provider 14, such as an E911 service, sends (200) an action signal 15, which is received at the device, and which awakens the device. It will be appreciated by those skilled in the art that the device may be active at all times, although this is thought to make unnecessary demands on the device's power source. Further, the device may also be locally activated by the person into which it is implanted, for example in a panic mode of operation.

When the device is active, it receives (300) positioning data or a signal that is used to determine position 17 from a positioning source 16 (discussed in greater detail below) and/or other data and transmits (400) a positioning signal 18 to the system provider, including emergency services or the police. The system provider, in turn, initiates a contact sequence or signal 19 by which the police or other appropriate authorities (such as a hospital or doctor in the case of a medical emergency) are contacted (500). Alternatively, the signal may be provided directly to the police et al.

Figure 2:
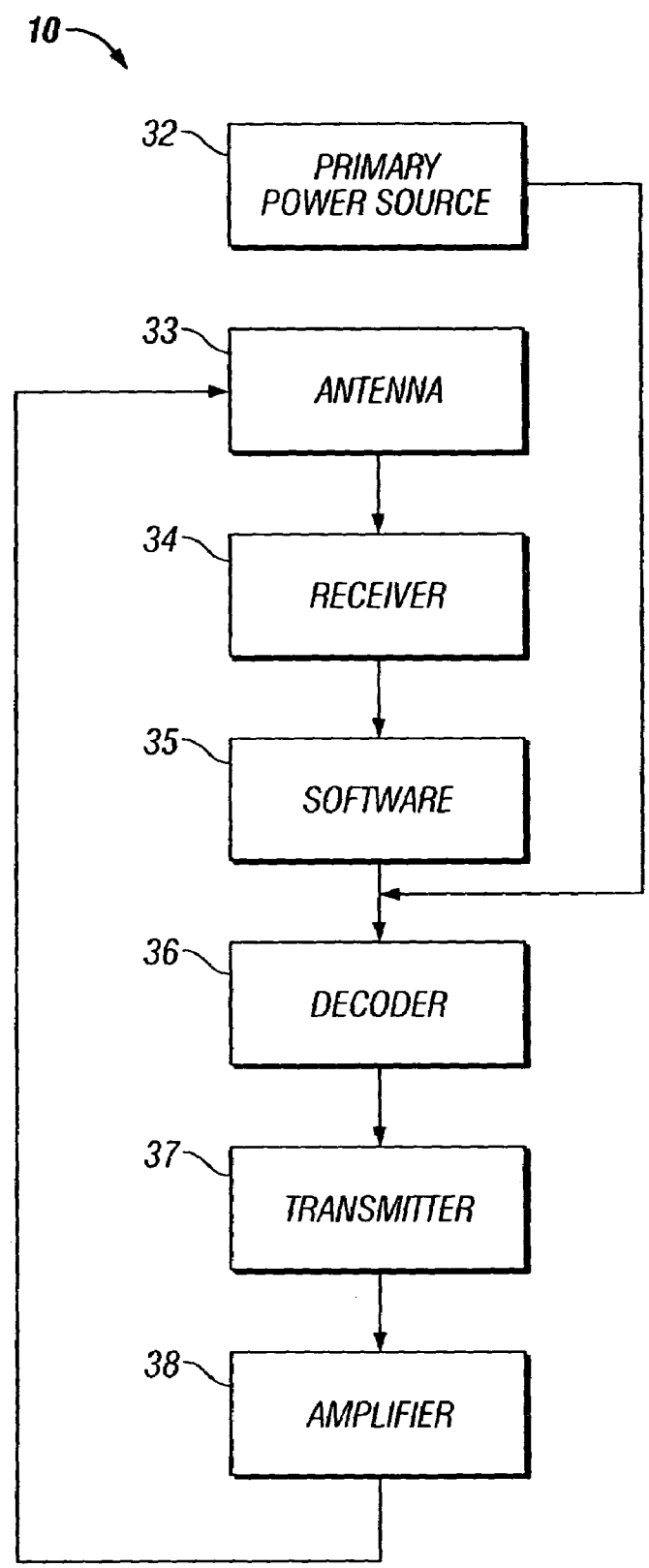
FIG. 2 is a block schematic diagram of an implant able device for use in a system for locating and tracking persons according to the invention.

FIG. 2 is a block schematic diagram of an implant able device 10 for use in a system for locating and tracking persons according to the invention. Each device has either an internal or external power source 32. Each device has an individual identifier (similar to that of cellular telephones, with each device having an individual telephone number) allowing for only that one device to be triggered into positioning-related activities. The triggering and positioning mechanisms function in conjunction with external systems which are completely or in part ground-based or satellite-based, air-based or water-based, and which use (but are not limited to) radiofrequency, cellular, sonar, microwaves, and/or light (visible and invisible), and/or television wave (analog and/or digital) technology, as discussed in greater detail below. Similar technology is used for device triggering to provide non-positioning information, such as monitoring of medical functions or the tracking of objects, e.g. monitoring the temperature of frozen foods while they are in transit.

The device preferably includes at least one antenna 33 which receives signals that are transmitted to the device and transmits signals from the device. The antenna and/or device may be shielded or partially shielded to address concerns about exposure of the person to signals generated by, or incidental to, the device.

A receiver 34 is provided, coupled to the antenna, which transforms signals received at the antenna in electrical impulses. System software 35 and a decoder 36 provide identification, control, and location information (see below). A transmitter 37 generates a signal, which is amplified by an amplifier 38, and thence coupled to the antenna for transmission in connection with operation of the device.

It will be appreciated by those skilled in the art that the foregoing description of the device is provided for purposes of example only and that many variations are known in the art or will be obvious to those skilled in the art. In this regard, the type of power source may comprise a battery, for example, a rechargeable battery, an inductive charging system for charging the battery, a mechanical or heat sensitive voltage generator, and the like; the antenna may be of a type suited for the location system chosen (see below), for example it could be an antenna that operates in an appropriate frequency range, for example, to receive GPS signals and/or cell telephone signals; likewise, the receiver and transmitter are provided in an appropriate frequency band, for example the cell telephone band. The functions of the software and decoder are also dictated by the specific embodiment of the invention implemented. A further description of the functions performed by these elements is provided below.

The described invention is an implant able device composed of biocompatible materials in all areas where contact with organic tissue occurs. Such materials are well known to those skilled in the art. The gross anatomic siting of the device includes any limb, the torso (including back and perineum), the neck, and the head.

Figure 3:
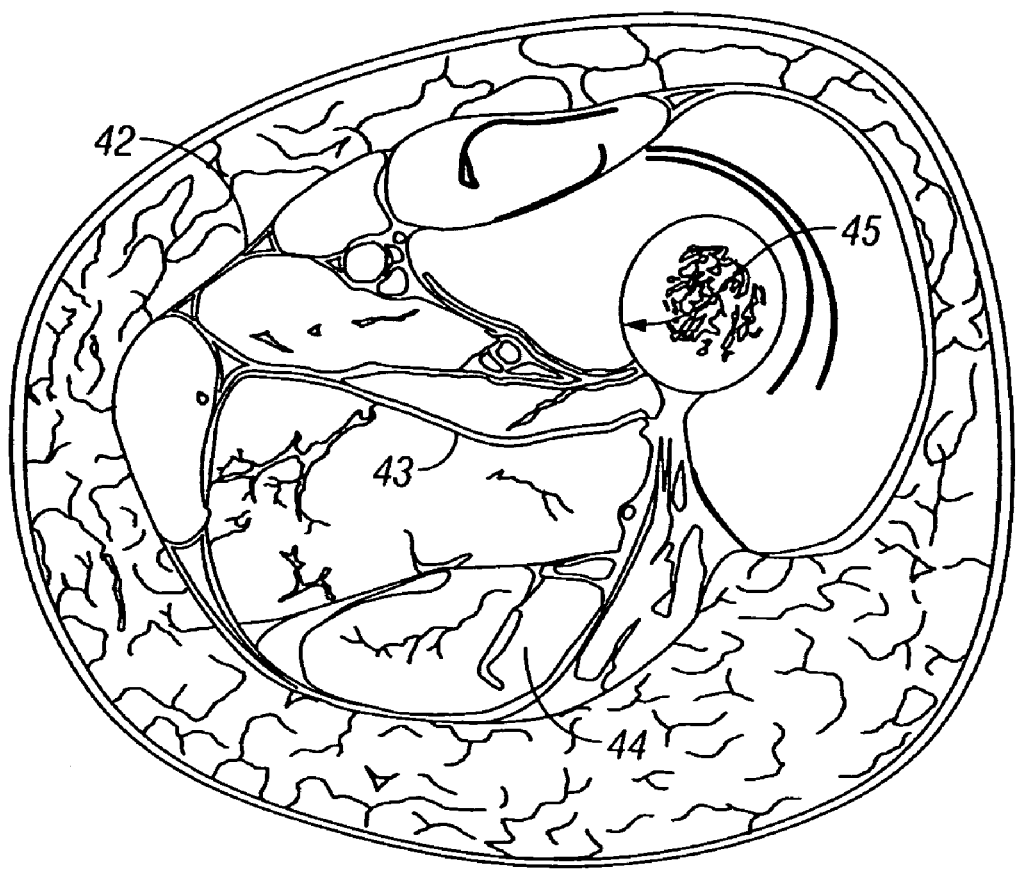
FIG. 3 is a diagram showing a supramuscular device implantation position, an intramuscular device implantation position, and a submuscular device implantation position, sagittal section of the intestinal tract and the uterus, according to the invention.

The presently preferred surgical anatomic siting of the device includes any of:

(1) Supramuscular (42). deep to the epidermis, dermis, and subcutaneous fat on or attached to muscle and/or muscle fascia (see FIG. 3). For example, such a location is currently used for implantation of commercially available buried intravenous access ports, which are positioned on (and attached to) the pectoralis major muscle fascia;

(2) Intramuscular (43, 44): for example, within or between the sartorius and adductor longus muscles of a limb (see FIG. 3);

(3) Submuscular (45): deep to a muscle (see FIG. 3). For example, such a location is currently used for implantation of commercially available artificial urethral and anal sphincter reservoirs, which are positioned deep to the rectus abdominus muscles, within the pre-peritoneal Space of Retzius, i.e. retropubic space. Another example being the retroperitoneal space.

Figure 4:
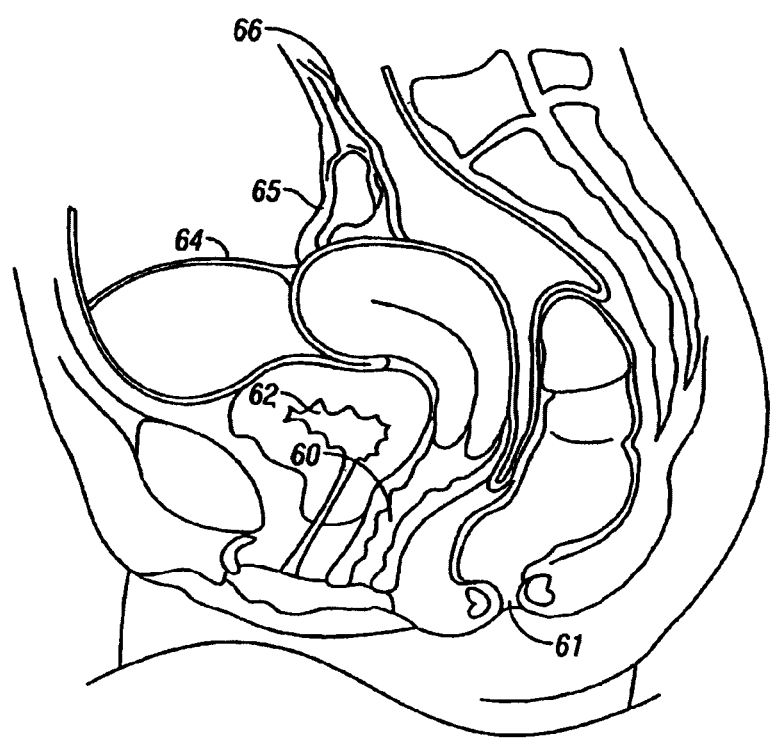
FIG. 4. is a diagram showing an intraluminal device implantation position, cross-section of the intestinal tract and sagittal section of the uterus, according to the invention.
Figure 5A:
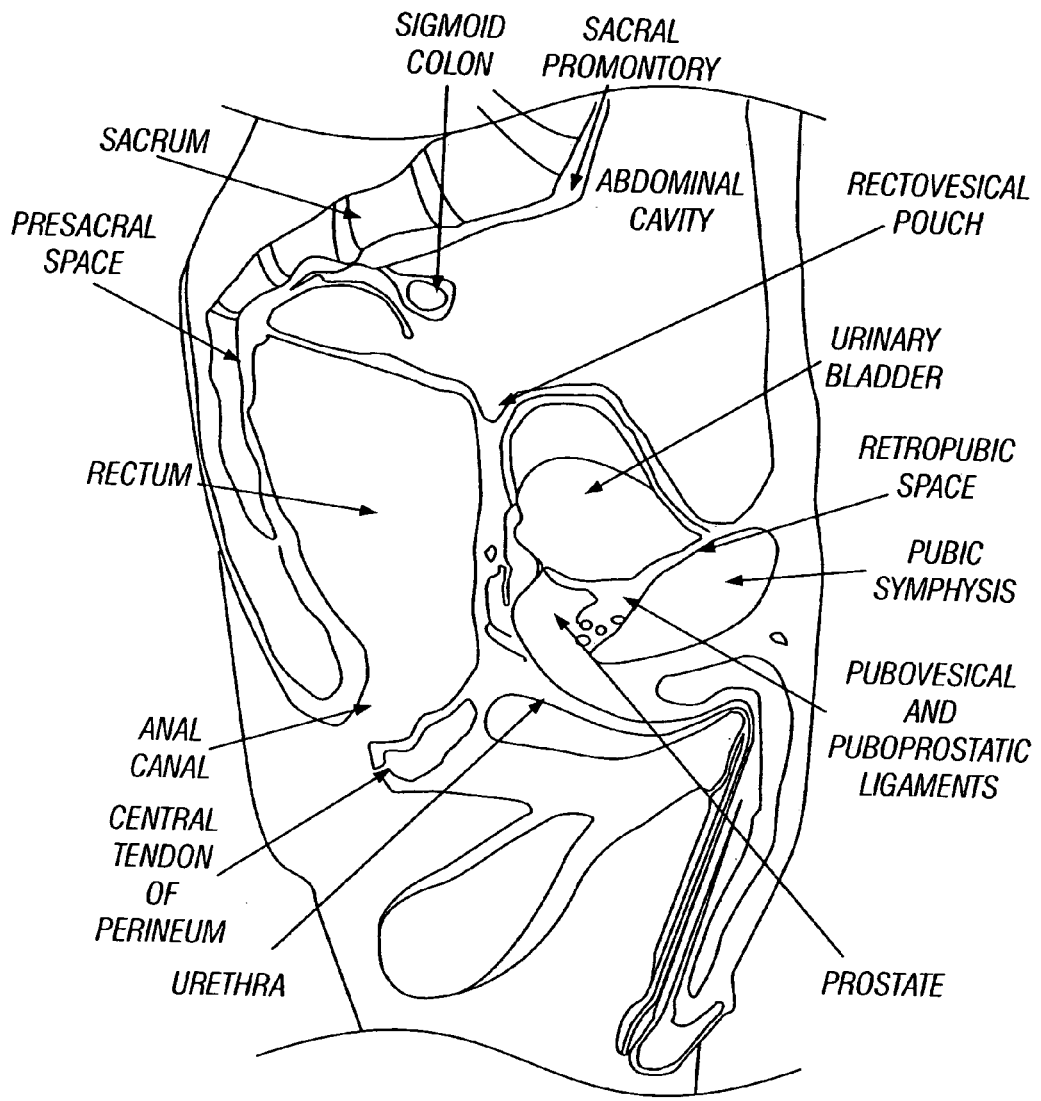
FIGS. 5a and 5b are diagrams showing intracavitary device implantation positions, according to the invention.
Figure 5B:
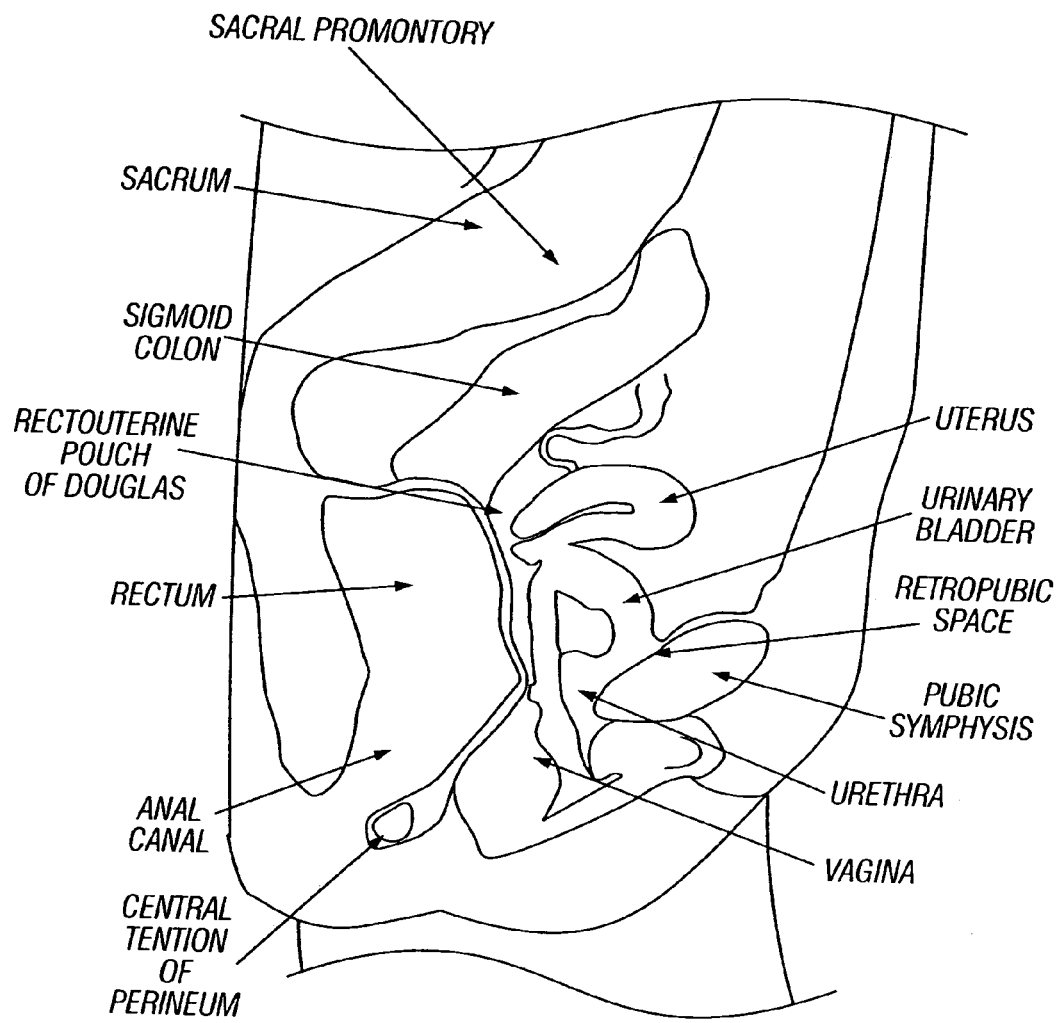
Figure 6:
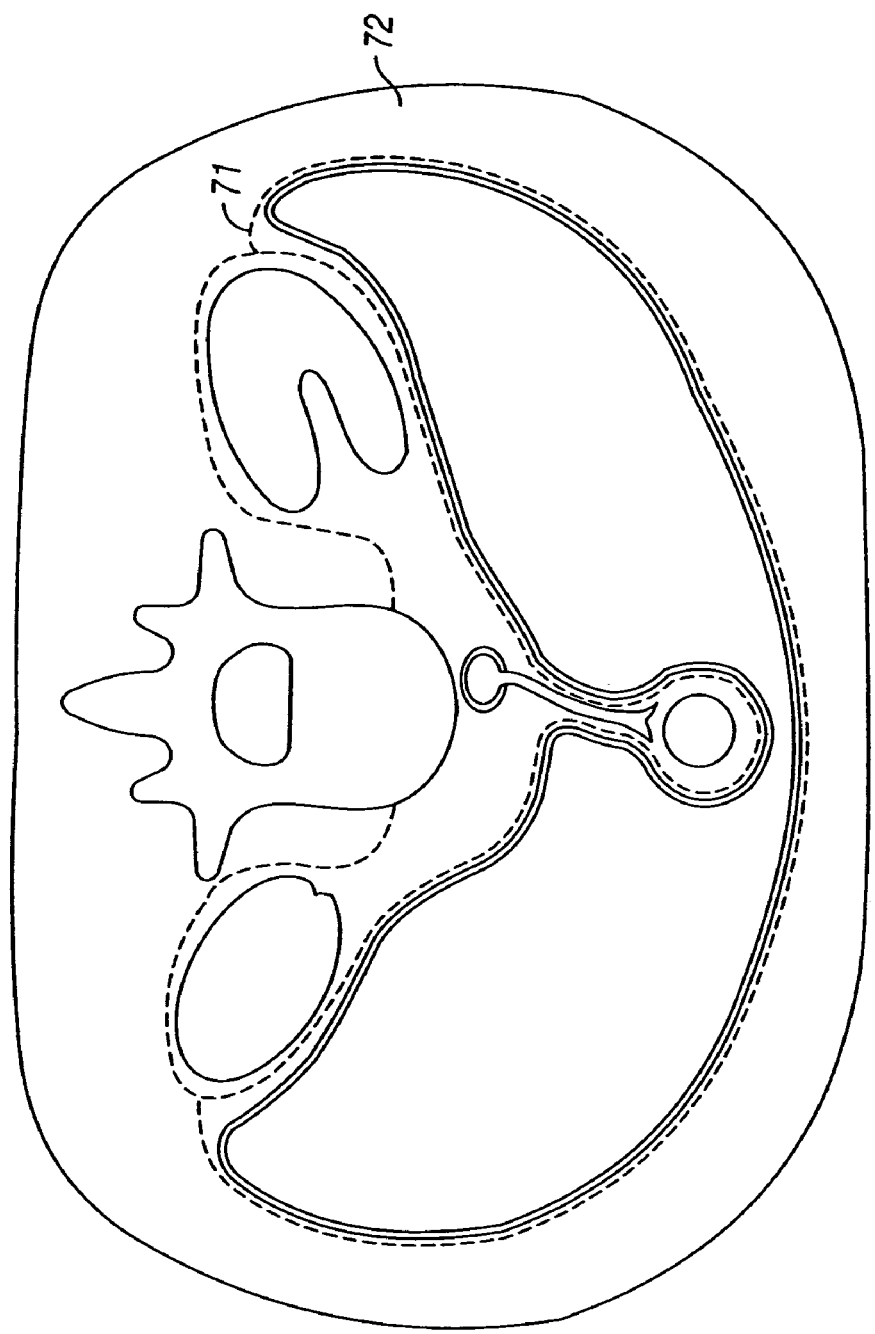
FIG. 6 is a diagram showing retroperitoneum and intracavitary device implantation according to the invention.
Figure 7:
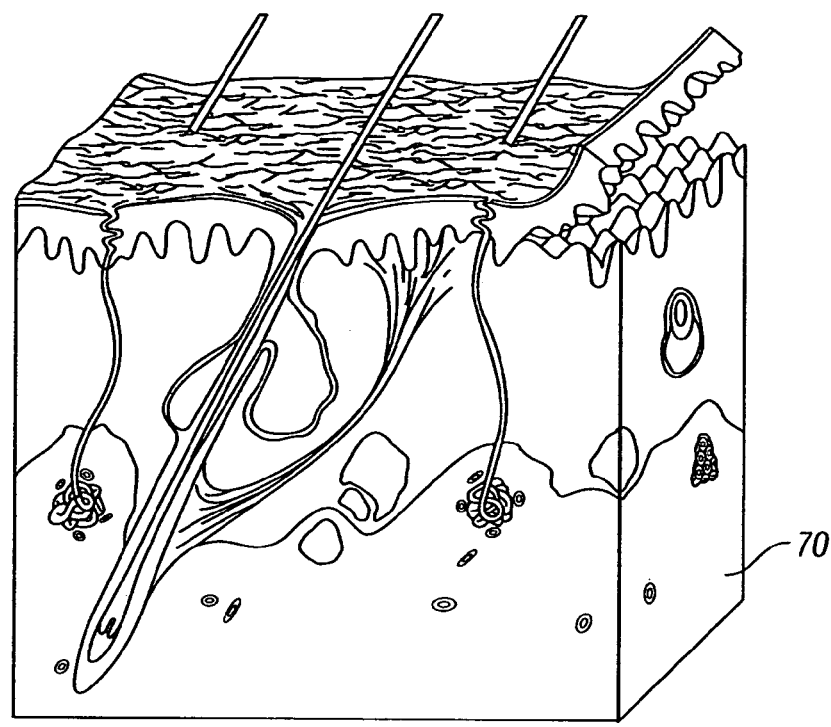
FIG. 7 is a diagram showing subcutaneous device implantation locations according to the invention.

(4) Intraluminal (60–66): within the lumen of an organ which has a naturally occurring orifice (see FIG. 4). For example, such a location is currently used for implantation of commercially available ingested video endoscopy capsule devices (gastrointestinal tract lumen) and intrauterine contraceptive devices (uterus lumen);

(5) Intracavitary (71, 72): intrathoracic or intraperitoneal (see FIGS. 5a, 5b, and 6). For example, such an intraperitoneal location is currently used for implantation of commercially available intraperitoneal dialysis catheters; and (6) Subcutaneous (70): in appropriate situations and individuals (mentally impaired elders, for example) in which the previously mentioned concerns associated with this location do not apply (see FIG. 7).

Implantation of the device may be via open surgical implantation, laparoscopic implantation, thorascopic implantation, endoscopic implantation (with or without visualization), direct vision-guided placement, or through the use of a placement device, procedure, and/or system developed for this purpose. For example, the device may be swallowed, as in a panic mode of operation.

In addition to these locations for implantation of the invention device, the device or a portion of the device, e.g. the power supply, antenna, a panic device, etc., can be attached external to the body (on the surface of the skin or on clothing, for example). For example, the device may include an external portion that is associated therewith, such as an inconspicuous piece of jewelry which, when removed from, or actuated by, the person to be tracked, triggers the device.

There are numerous advantages to the non-subcutaneous locations for implantation of the described device, including (but not limited to):

(1) The implanted device is not easily located by the abductor and, therefore, not vulnerable to simple and safe removal. Even if located, removal would likely be impossible for the non-surgical abductor. Even if possible, such removal would likely place the victim at significant risk, which is counter to the abductor's goal in the overwhelming majority of abduction cases (see Family Abductions and Acquaintance Abductions);

(2) Removal of the implanted device by a runaway juvenile would likely be impossible. Even if possible, such removal would likely place the runaway at significant medical risk, which is counter to the runaway's goal of safe escape and survival from parents or guardians;

(3) Relative to implantation just beneath the skin, implantation of the device in the supramuscular, intramuscular, submuscular, intraluminal, or intracavitary position provides significantly greater protection to the device from the accidental damage which is likely to occur with daily physical activities, especially in juveniles;

(4) Relative to implantation just beneath the skin, implantation of the device in the supramuscular, intramuscular, submuscular, intraluminal, or intracavitary position provides a significantly more acceptable cosmetic result because there is no lump created by the device. When an incision is required for placement (supramuscular, intramuscular, submuscular, and intracavitary positions), that incision is minimal and easily hidden within an area normally covered by body hair or clothing, for example. Intraluminal placement requires no incision. These options are all cosmetically superior to subcutaneous implantation; and (5) Implantation of the device in the supramuscular, intramuscular, submuscular, luminal, or intracavitary position allows for the use of larger, more sophisticated, and more efficacious positioning devices and antennae, as well as more durable power sources, without the exposure to accidental damage and the less favorable cosmetic result associated with implantation immediately beneath the skin.

Current Implanted devices relying on a GPS antenna within the device are unable to receive GPS signals at present.

DEVICE

External Design of Device

1. Device Components Design

The device may consist of one component or may consist of multiple components (modular device design). One example of a modular device includes a main component containing all circuits and a power supply attached to a second component serving as an antenna.

2. Device Form

One or more device components (modular device design) may take one of a variety of forms, including, but not limited to, forms similar to:

Commercially available implanted neurostimulators
Commercially available implanted cardiac pacemakers
Commercially available implanted vascular access ports.

3. Device Fixation

One or more device components (modular device design) may have associated fixation features allowing for fixation (with suture, for example) to surrounding tissue structures. Examples of fixation features can be found on commercially available implanted vascular access ports.

4. Device Shielding

The device may have materials incorporated into the design serving to shield certain body regions from device energy emission. For example, shielding material over one surface of the device may serve to prevent energy transmission posteriorly within the body.

5. Antenna Design

The antenna may be the device package (casing) itself, incorporated into the device package, attached to the device package, or separate but connected to the device package (modular device design). The antenna may take one or more of a variety of forms, including (but not limited to) a rod, flat panel, sheet, and/or coil.

Further to the discussion above in connection with FIG. 2, the following is noted:

Primary Power Source 32. In the preferred embodiment, the device comprises an internal, self-contained primary power source, which is remotely rechargeable, through inductance. In another embodiment, the primary power source is external, and is also part of the activation mechanism, where, when removed from a predetermined proximity, the lack of the primary power source triggers a secondary or backup power source to initiate a notification signal. In another embodiment, the primary power source is recharged using any other remote recharging method. In another embodiment, the primary power source is recharged using any other body electrical or body mechanical energy generation method. In another embodiment, the primary power source is non-rechargeable.

Antenna 33. In the preferred embodiment, the device contains an antenna to assist in receiving an activation signal and/or sending a notification signal. In another embodiment, the device does not require the assistance of an antenna. In another embodiment, the device does not require an antenna as part of the device itself, but utilizes the body or some other pre-existing item/entity for the antenna.

Receiver 34. In the preferred embodiment, the device contains a transceiver that is capable of detecting a unique incoming signal. The transceiver is preferably dormant or semi-dormant until activated. In another embodiment, the device contains separate receiver and transmitter components. In another embodiment, the transceiver or receiver is not dormant, but continuously or regularly or patterned polls for a signal after every predefined time period. This latter embodiment conserves power by providing dormancy between polls. In one embodiment, spread spectrum techniques may be used.

Software 35. In another embodiment, the device contains dynamic software programming, which allows the device to evolve over a specified time. This evolution may take on the form of any number of transitions from an active receiver, which sends out a distress signal if the device moves beyond a specified distance from an external signal transmitter, i.e. for infants and toddlers, to a passive receiver, which requires a customized signal be sent to the device, at which time the device activates and begins transmitting a distress signal, i.e. for older children. In another embodiment the dynamic software programming is triggered by an external signal (local or remote) and places the device in a pre-configured state. In another embodiment, the device is a single software phase device which is always active, always passive, or somewhere in between. In another embodiment, other aspects of the device's performance are programmable, such as, but not limited to, the type of signal to which the device responds, the type of signal the device transmits upon activation, or a permanent shutdown mode. In another embodiment, the dynamic software programming is used to trigger an optional device stimulation feature, such as a slight vibration or very mild shock to the carrier to alert them that someone responding to their notification or distress signal is approaching.

Decoder 36. In the preferred embodiment, the device software is capable of decoding any pre-defined unique signals received and carries out any pre-configured instructions. In another embodiment, the device contains separate decoding electronics to decipher a unique signal that it receives. For example, a trigger protocol is provided that comprises a second signal having that device ID or is provided within a certain time.

Transmitter 37. In the preferred embodiment, the device contains a transceiver that is capable of transmitting a notification signal. The transceiver is preferably dormant or semi-dormant until activated. In another embodiment, the device contains separate receiver and transmitter components. In another embodiment, the transceiver or transmitter are not dormant, but continuously send a notification signal after every predefined time period. In such embodiment, a missed signal, for example when the person is out of range, triggers an alarm. Such embodiment is useful, for example, for assuring that a person stays within a defined location, such as a felon who is being electronically monitored. In another embodiment, the device contains a transponder for signal handling Amplifier 38. In the preferred embodiment, the device is capable of receiving and transmitting without the necessity of a signal amplifier. In another embodiment, the device contains an amplifier for the receipt and/or transmission of a signal.

Activation and Tracking System

Figure 8:
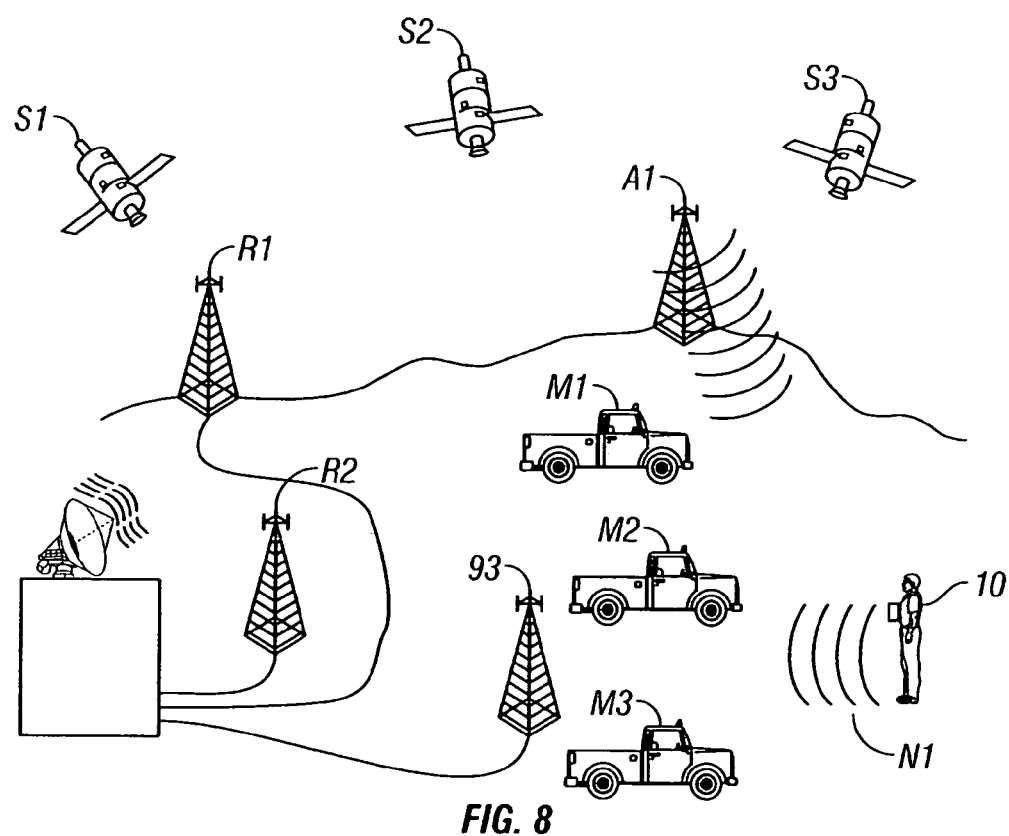
FIG. 8 is a block schematic diagram showing an activation and tracking system according to the invention.

FIG. 8 is a block schematic diagram showing an activation and tracking system according to the invention.

Activation Signal. In the preferred embodiment, the waveform used to activate the device (A1) is a terrestrial delivered cellular signal due to its availability and commonality. In another embodiment, the activation waveform is delivered extra-terrestrially. IN another embodiment, the signal is air-based or water-based. In another embodiment, the activation waveform is digital television based due to its effective wave propagation characteristics. In another embodiment, the activation waveform is radiofrequency based. In another embodiment the, activation waveform is any other frequency based. Further, combination of the foregoing techniques may be used.

Return/Notification Signal. In the preferred embodiment, the waveform used by the device as a notification signal (N1) is terrestrial, air-based or water-based, in nature and GSM based. In another embodiment, the notification waveform is extra-terrestrial in nature. In another embodiment, the notification waveform is IDEN, CDMA, TDMA, or radio frequency based. In another embodiment, the notification waveform is GSM based. In another embodiment, the notification waveform is any other frequency based or may be sound, e.g. sonar or light based. In another embodiment, the notification signal comprises a scrambling signal with a unique identity, which is detected by a cable television system, cellular telephone system, or another signal based system. Further, combination of the foregoing techniques may be used.

Signal Tracking. In the preferred embodiment, the return/notification signal is tracked through a series of terrestrial based receiving stations (R1, R2, R3 . . . ). In another embodiment, the notification signal is tracked through a series of extra-terrestrial based satellites systems (S1, S2, S3 . . . ). In another embodiment, the notification signal is tracked through a series of mobile receivers (M1, M2, M3 . . . ) which may be air, water, or land based, or a combination thereof. In another embodiment, the notification signal is a scrambler and is tracked through signal inconsistencies by either terrestrial based receiving station(s) or extra-terrestrial based satellite(s). Further, combination of the foregoing techniques may be used.

There are presently three preferred terminal based positioning techniques and variants thereof that may be used in connection with the herein disclosed invention:

(1) Global Positioning System (GPS);

(2) Network assisted GPS (AGPS); and (3) Enhanced Observed Time Difference (E-OTD)

GPS. The global positioning system (GPS) is a satellite-based radio-navigation system developed and operated by the U.S. Department of Defense (DOD). GPS provides the user with their three-dimensional position, their current velocity, and the exact time. The GPS system consists of 24 satellites orbiting the earth in six circular orbits. The satellites are arranged, so that at any one time there are six satellites within range of a GPS receiver. The control segment of the GPS system consists of one master control station in Colorado USA, with five ground control stations and three ground antennas located around the world. The monitor stations passively track all the satellites in view. A sample of each of the satellites broadcast signal is continuously taken. These samples are then forwarded on to the master control station, which calculates extremely precise satellite orbits. The orbit calculations are formatted into navigation instructions, which are uploaded to the individual satellites via the ground antennae. At the same time each of the satellites is continuously broadcasting an exact position and time signal. The GPS receiver receives messages from at least four satellites and measures the time delay for each signal. From these values the GPS unit can calculate the user position and velocity.

Differential GPS. Differential GPS is a technique that is used to increase the accuracy of GPS receivers to between one to three meters. The technique involves placing a GPS receiver, i.e. a reference receiver, in a known physical location. The reference receiver collects data from all the satellites in view and performs error corrections on the signals checking the actual location against the broadcast location. These corrections can be either recorded (used for post-processing of signals) or broadcast in real-time via radio. To benefit from the broadcast of a DGPS signal, a GPS receiver must be equipped with a data port connected to a radio receiver. Furthermore, the GPS unit must be within approximately 150 km of a DGPS signal transmitter.

Network assisted GPS (AGPS). A GPS receiver can be integrated into the circuitry of a mobile telephone/device with minimal price impact on the consumer. Such system is well suited for use in connection with the implant able device herein disclosed. It should be noted that there are problems with GPS that make it unsuitable for mobile positioning. These problems include:

(1) A high time-to-first-fix. A GPS unit can take between 30 seconds and several minutes to acquire and track satellites initially.

(2) Low sensitivity to signal attenuation, blockage, and multipath interference. A GPS unit does not produce accurate results, if any, in many difficult environments when the GPS signal is weak, e.g. in an urban canyon, inside a building, or under dense foliage. This limits the accessibility of the implant able device somewhat when a person to be located and/or tracked is indoors, for example. Multipath interference occurs when signals get refracted for some reason, e.g. atmospheric layers, clouds, and buildings, and arrive out of phase with the original signal, thus canceling it. Many GPS units have up to twelve parallel GPS signal receivers to minimize these effects.

(3) Power inefficient. GPS keeps a continuous track on the viewable satellites once a first fix is obtained. There is also a high overhead, in terms of power, of running up to twelve parallel receivers. For many mobile telephone/device users, this power drain may outweigh the benefit of having terminal-based positioning. This is an especially important consideration in connection with the implant able device herein disclosed.

(4) Accuracy. GPS is typically accurate to 20 meters. Because a mobile device is always connected to the mobile network, there is no need for a separate DGPS receiver. The DGPS signal can be sent via the mobile network.

Figure 9:
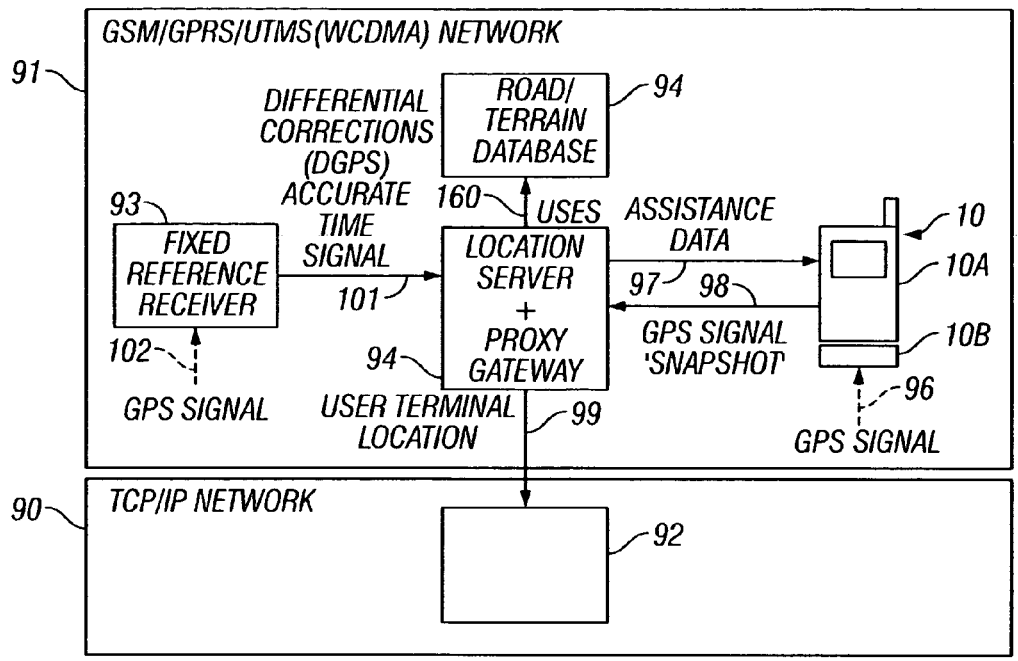
FIG. 9 is a block schematic diagram of a network assisted GPS positioning system for use in a system for locating and tracking persons according to the invention.

Network Assisted GPS attempts to solve these problems. Most AGPS solutions do this by using the distributed architecture shown in FIG. 9. GPS processing is distributed between a reference receiver 93, a location server 94, and the GPS enabled user terminal, in this case the implant able device 10.

Fixed Reference Receiver. The fixed reference receiver acts as a DGPS beacon. It is a normal GPS receiver that receives a GPS signal 102, but because its physical location is known, it can calculate the differential corrections that need to be applied to the signal sent from the user terminal to the location server. These corrections 101, along with an accurate time signal, are continuously, cyclically, or periodically sent to the location server.

User Terminal. The user terminal, i.e. the implant able device 10, is a mobile device connected to a digital mobile network. The device contains a GPS receiver 10b that is integrated into its circuitry 10a. When a person needs to be located, the location server sends the device assistance data 97. The request for a user terminal location comes from either the location server or a third party application 92, depending upon where the person locating and tracking system resides. The assistance data consist of satellite information on the all the satellites in view in the terminals approximate location and the Doppler offsets of each of the satellites. The location sever uses the location of the base station as the approximate location of the user terminal. The user terminal then takes a snapshot of the GPS signal 96, pre-processes it, and returns basic GPS measurements, along with statistical values characterising the signal environment. This GPS signal snapshot 98 is then returned to the location server.

Location Server. The GPS snapshot signal received by the location server from the device is then further processed to remove errors, such as multipath interference and atmospheric delays. The DGPS data from the fixed reference receiver are also applied at this point. The device's precise latitude, longitude, altitude, speed, and bearing are then provided to the application that requested it, e.g. to an emergency tracking service. The location server can use a terrain database 94 to refine the position data further. Uses 100 of the terrain database include snapping location (longitude, latitude, and altitude) to the nearest road. This is used for a tracking system implemented in accordance this the invention to help locate a person, for example a kidnapped child.

The GPS portion of the invention 91 may reside in one network, while the actual tracking application may reside in another network, such as a TCP/IP network 90, in the form of a module outside the domain of a mobile network provider.

Figure 10:
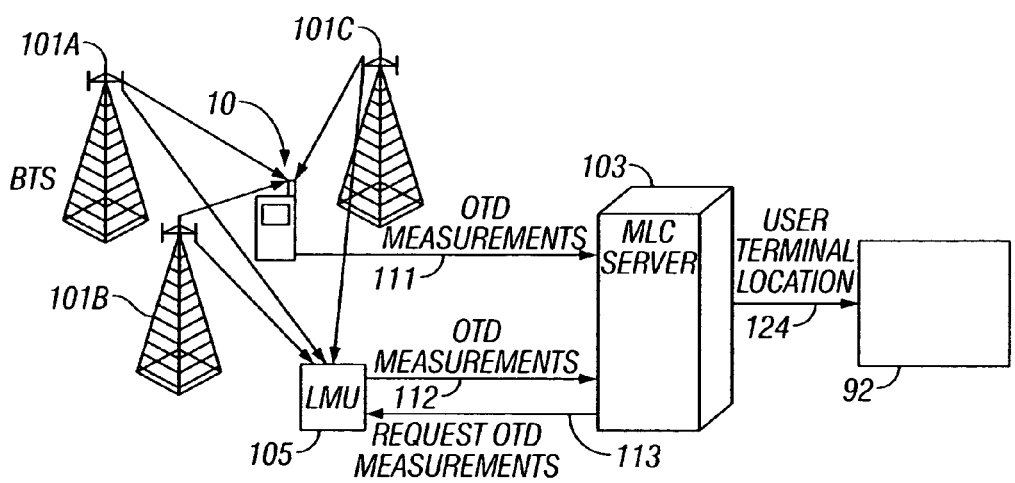
FIG. 10 is a block schematic diagram of an enhanced observed time difference positioning system for use in a system for locating and tracking persons according to the invention.

Enhanced Observed Time Difference (E-OTD). E-OTD requires only a software modification to the user terminal. This means that the device may be readily produced from a standard base technology, such as a cell telephone. However, to run the E-OTD algorithms, E-OTD enabled terminals need additional processing and memory capacity. As shown in FIG. 10, E-OTD consists of the following procedures:

(1) The device measures control signals from at least three surrounding base transceiver stations (BTS) 101a–101c.

(2) The device measures the observed time difference (OTD) between pairs of incoming control signals. These data 111 are put in a message and sent to a central server (called the mobile location center or MLC) 103.

(3) When the MLC receives the message, it contacts the relevant location measurement unit (LMU) 105 and requests 113 the OTDs of the control signal from all the BTSs monitored by the LMU. An LMU is essentially a receive-only GSM antennae and must be deployed for every four BTSs. The MLC knows the physical location of the BTSs and the physical location of the LMU. Using the difference in the OTDs of LMU 112 and the device 111, the MLC can calculate the physical location of the device. As in AGPS, this location information 114 is sent party application, i.e. the person tracking and locating service 92. The accuracy of this system in GSM networks is between 60 meters in rural areas and 200 meters in bad urban areas (weak signal reception due to blockage and interference).

Network Based Positioning Techniques. Network based positioning techniques, may not require changes to be made to the device to find its location. Therefore, the major benefit of network-based positioning systems is backward compatibility. With network based positioning, all modifications are made to the network, with no impact on the end user.

Figure 11:
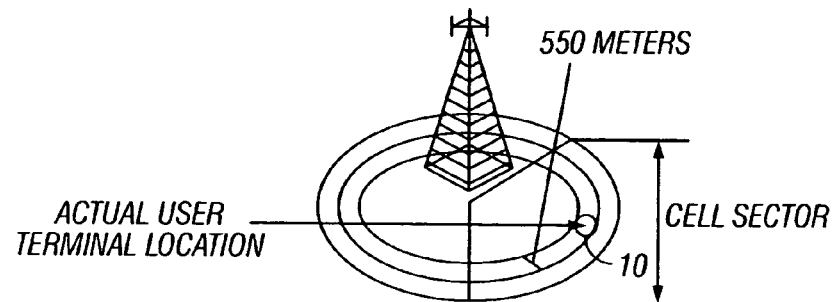
FIG. 11 is a block schematic diagram of a cell global identity and timing advance positioning system for use in a system for locating and tracking persons according to the invention.

Cell Global Identity and Timing Advance (CGI+TA). The CGI+TA technique works by measuring two existing parameters in the GSM system. The cell global Identifier (CGI) is a unique identifier for each cell sector in the network. The timing advance (TA) parameter is the based on the access delay between the beginning of a time slot and the arrival of bursts from the mobile terminal. Because the access delay is proportional to the distance from the base transceiver station (BTS), an estimate of the user radius about the BTS can be calculated. Currently the TA value can only be calculated in increments of 550 meters. By combining the CGI and TA parameters, a user terminal position can be estimated as an arc 550 meters wide within a particular cell sector. As can be seen in FIG. 11 the telephone can be located to an arc 550 meters wide. The accuracy for this technique depends on three factors:

(1) The distance the user terminal is from the BTS: When the user terminal the radius of the arc is smaller, thus more accurate estimate is given;

(2) The radius of the cell; and (3) The size of the sector. In a typical GSM system cell radii vary from 100 meters to 30 km. This technique is the least accurate of all the positioning techniques, but requires no modifications to the systems hardware or software.

Figure 12:
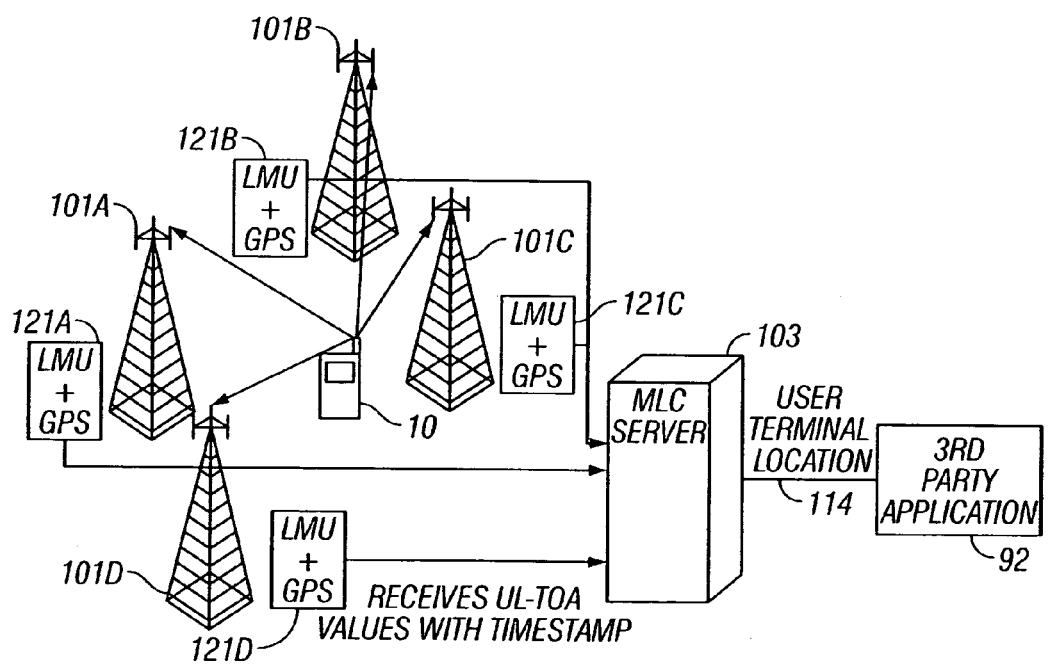
FIG. 12 is a block schematic diagram of a time difference of arrival positioning system for use in a system for locating and tracking persons according to the invention.

Time Difference of Arrival (TDOA). The Time Difference of Arrival (TDOA) technique (see FIG. 12) is essentially the same technique as E-OTD, except that it is done in the opposite direction. That is, the observed time difference (OTD) calculations are done at at least four different base stations 101a–101d instead of at the device 10. Each LMU 121a–121d is equipped with a GPS receiver to receive the time signal, which is broadcast continuously by the GPS satellites. Alternative timing references, such as rubidium oscillators could be used. Clock drift arises, but can be solved using a distributed time synchronization algorithm.

Each LMU measures the uplink time of arrival (UL-TOA) of a continuous stream of data from the user terminal. This value along with a precise timestamp is sent to the MLC server. The MLC calculates the time difference of arrival between pairs of UL-TOA values, taking into account the timestamps of each of the UL-TOA values. Because the geographical location of each base transceiver station is known, an estimate of the location of user terminal can be calculated. The TDOA technique is quite costly from the network provider's point of view because an LMU+GPS receiver must be installed in practically every base transceiver station. Each of the LMUs must also be connected via a landline to the MLC server. The system is not able to give an estimate, or at least give an inaccurate estimate, if the user terminal cannot be tracked by at least four individual base transceiver stations. However, for a network based solution the accuracy is relatively quite good, i.e. approx. 50 meters in rural location and 150 meters in bad urban areas.

Angle of Arrival (AOA). The angle of arrival positioning technique requires only two base transceiver stations with antennae arrays installed to position a user terminal. An antennae array is a arrangement of antennae in a precise, fixed pattern. Given a known operating frequency, and known antenna spacing, by measuring the phase or phase difference on a number of antennas, the angle of arrival of a plane wave can be deduced. By measuring the angle of arrival at a two or more BTSs, the intersection point of the bearing vectors can be calculated. This intersection is the estimated location of the user terminal. AOA is very sensitive to multipath interference and accuracy is reduced the further the user terminal from the BTS. Typically, AOA is used in conjunction with the TDOA technique to improve accuracy, but due to its sensitivity to multipath interference it is not robust enough to use on its own.

The Four System Components

| | |
|---|---|
| 1. The parent/guardian of the missing child | "P/G" |
| 2. The System Provider | "PSP" |
| 3. 911 Emergency Services | "911" |
| 4. The personal locator device | "R" |

Overview of System Function
　1. P/G reports of missing child
　2. R is activated
　3. R provides location
　4. 911 provides emergency recovery
　5. P/G/ are notified A. Options for Initiating the System
　1. P/G contacts PSP
　2. P/G contacts 911

B. Steps following Initiation of the System

I. If the PSP is contacted by the P/G:
　1. PSP activates R
　2. PSP contacts 911 (and 911 activates R)
　3. PSP activates R and contacts 911

II. If 911 is contacted by the P/G:
　1. 911 activates R
　2. 911 contacts PSP (and PSP activates R)
　3. 911 activates R and contacts PSP C. Steps following Activation of R
　1. R provides location to PSP
　2. R provides location to 911

D. Steps following Providing of Location
　1. PSP provides location to 911 (and 911 provides emergency recovery)
　2. 911 provides emergency recovery E. Informing th Par nt/Guardian
　1. PSP contacts P/G
　2. 911 contacts P/G
　3, PSP and 911 contact P/G

EXAMPLES OF FUNCTIONING SYSTEMS

Example #1

1. P/G contacts PSP
2. PSP activates R
3. R provides location to 911
4. 911 provides emergency recovery
5. 911 contacts P/G Example #2

1. P/G contacts PSP
2. PSP activates R
3. R provides location to 911
4. 911 provides emergency recovery
5. 911 contacts PSP
6. PSP contacts P/G

Example #3

1. P/G contacts PSP
2. PSP contacts 911
3. 911 activates R
4. R provides location to 911
5. 911 provides emergency recovery
6. 911 contacts P/G

Example #4

1. P/G contacts PSP
2. PSP contacts 911
3. 911 activates R
4. R provides location to 911
5. 911 provides emergency recovery
6. 911 contacts PSP
7. PSP contacts P/G

Example #5

1. P/G contacts PSP
2. PSP activates R
3. R provides location to PSP
4. PSP provides location to 911
5. 911 provides emergency recovery
6. 911 contacts P/G

Example #6

1. P/G contacts PSP
2. PSP activates R
3. R provides location to PSP
4. PSP provides location to 911
5. 911 provides emergency recovery
6. 911 contacts PSP
7. PSP contacts P/G

Example #7

1. P/G contacts 911
2. 911 contacts PSP
3. PSP activates R
4. R provides location to PSP
5. PSP contacts 911
6. 911 provides emergency recovery
7. 911 contacts P/G

Example #8

1. P/G contacts 911
2. 911 contacts PSP
3. PSP activates R
4. R provides location to PSP
5. PSP contacts 911
6. 911 provides emergency recovery
7. PSP contacts P/G

Example #9

1. P/G contacts 911
2. 911 contacts PSP
3. 911 activates R
4. R provides location to PSP
5. PSP contacts 911
6. 911 provides emergency recovery
7. 911 contacts P/G

Example #10

1. P/G contacts 911
2. 911 contacts PSP
3. 911 activates R
4. R provides location to PSP
5. PSP contacts 911
6. 911 provides emergency recovery
7. PSP contacts P/G

Example #11

1. P/G contacts 911
2. 911 activates R
3. R provides location to PSP
4. PSP contacts 911
5. 911 provides emergency
6. 911 contacts P/G

Example #12

1. P/G contacts 911
2. 911 activates R
3. R provides location to PSP
4. PSP contacts 911
5. 911 provides emergency
6. PSP contacts P/G

Example #13

1. P/G contacts 911
2. 911 contacts PSP
3. PSP activates R
4. R provides location to 911
5. 911 provides emergency recovery
6. 911 contacts P/G

Example #14

1. P/G contacts 911
2. 911 contacts PSP
3. PSP activates R
4. R provides location to 911
5. 911 provides emergency recovery
6. 911 contacts PSP
7. PSP contacts P/G FIG. 13 is a flow chart showing operation of the device according to the invention.

Figure 13:
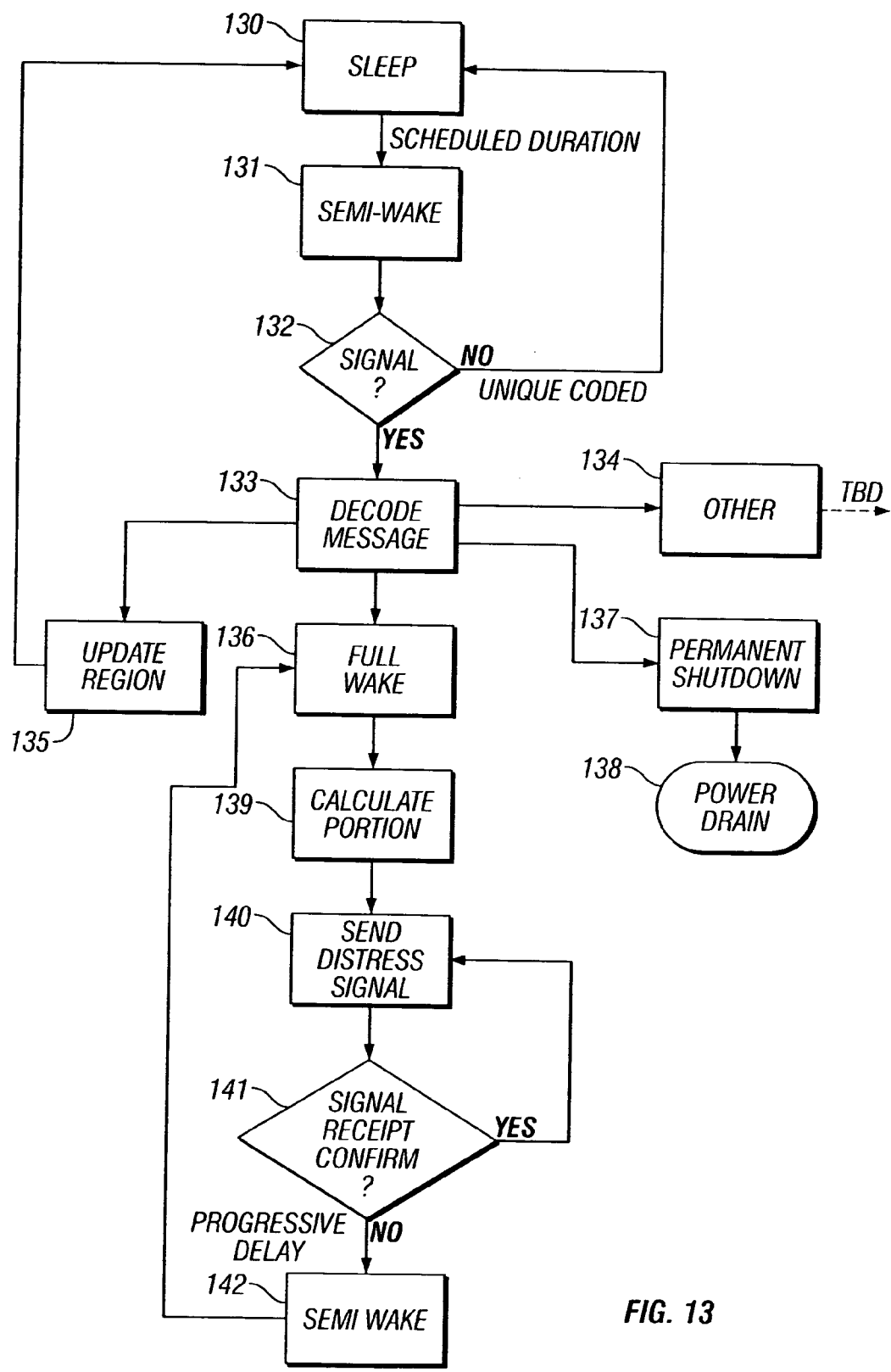
FIG. 13 is a flow chart showing operation of the device according to the invention.

In FIG. 13 the device is first in a sleep state 130, which may be a scheduled duration. The device will periodically enter a semi-wake state 131 and pull for a trigger signal 132. If no such signal is received the device will return to the sleep state. If a signal is received and the signal is coded as required then a decode message sequence will begin 133. At this time the device may perform such functions as updating the device for travel to a new region 135, a permanent shutdown 137 due to power drain 138, or such other functions as may be desired 134. However, the main purpose of sending such trigger signal would be to bring the device to a full wake condition 136 such that the device may calculate position 139 and send a distress signal 140. Optionally, a signal may be received confirming that the distress has been properly acknowledged 141; if, however, such signal is not received, the progressive delay may, for example, be entered, at which time a wake signal may be sent 142 bringing the device again to a full wake state 136 and thereby activating the device to determine its position and to send a further distress signal. The signal itself may be transmitted to the device or it may be the result of some user action, for example the user may be wearing a piece of jewelry with a proximity switch, such as a magnetic read switch or local oscillator which when activated or moved from the proximity of the user's body causes the device to go to full wake state.

Although the invention is described herein with reference to the preferred embodiment, one skilled in the art will readily appreciate that other applications may be substituted for those set forth herein without departing from the spirit and scope of the present invention.

For example, while the invention is taught to have applications in the location and tracking of persons, presumably after they have gone missing, when an activation signal is sent to the implant able device to begin locating and tracking the person, the invention is readily applicable to maintaining contact with persons, for example within a defined geographic region. Thus, a felon monitoring system may be implemented in accordance with the invention herein. When a felon leaves a prescribed area, or enters a proscribed area, the implant able device is activated to alert the appropriate authorities of the felon's wayward behavior. Because the device is implanted in the person, it can also provide a shock, vibration, or other warning to alert the person of the transgression. The shock or other alert may be progressive, such that a person is subjected to a shock of increasing magnitude as he leaves a zone of confinement or enters a forbidden zone.

An alert can also be broadcast to the person when urgent contact is required. Thus, the device may vibrate or provide other notice when an emergency occurs that requires the person's immediate attention.

The invention may also be used in connection with a tracking system to track several persons at the same time, for example to track soldiers on a battlefield, employees within an enterprise campus, or business travelers within a geographic region.

The device may also be activated periodically to take a series of fixes on a person's location, even if an emergency, such as a kidnapping, has not occurred.

The device may also include various sensors to monitor the person's body functions and the like, or it may include a microphone or similar device for monitoring acoustic information, thereby permitting the person to talk to a remote location.

The device is taught to be an implant able device, but may also be an embedded device, i.e. positioned subcutaneously.

Further, the device may operate in any of several bands and in accordance with any of several protocols to allow locating and tracking a person who is moving, for example, across international borders, where different frequency bands and/or protocols are used for communication.

Additionally, the device may be field programmed, for example, to allow different frequencies or protocols to be activated, to allow a change of the unique identity of the device, and/or to interrogate the device for monitored and/or stored information. For example, the device may also include storage for such information as blood type, identification information, a picture of the person, and the like, which information may be retrieved when the device is either interrogated or activated.

The device may have a variety of programmable models including, but not limited to:
Sleep mode duration;
Wake mode activities;
Signal polling duration;
Regional time setting;
Regional activation adjustment, e.g. to reduce power drain.
Device functionality assessment/adjustment; and
Permanent shutdown mode.

In the event of a false/inadvertent triggering event, the device can assess and confirm whether the trigger was inadvertent, and can be either internally reset or reset through remote signaling, i.e. through the systems provider, etc., or both.

In the event that a rechargeable power supply is used, the device can be recharged through inductance, or other means, and at any interval necessary.

Also, the device may be associated with any of various objects. For example, a valuable object or objects may be monitored, periodically located and tracked, and otherwise supervised in transit. Such monitoring may include the collection and transmission of ambient information, such as temperature.

Further, more than one device may be provided, where the devices may communicate with each other. One of such devices may be an extermary or device.

Further, the device may not include positioning mechanisms, but may be used as a communication-only device for conveying information, for example when polled.

Accordingly, the invention should only be limited by the claims included below.

The invention claimed is:

1. An implantable apparatus for use in a system for locating and tracking a person, comprising:
   a power source;
   an individual identifier that allows for only said device to be triggered into positioning-related activities;
   a triggering and positioning mechanism that functions in conjunction with external systems which are completely or in part ground-based, air-based, water-based, or satellite-based, or a combination thereof and which use, but are not limited to, any of radiofrequency, cellular, sound, light, and/or television wave analog and/or digital technology, for positioning and device triggering to provide any of positioning and non-positioning information;
   a receiver;
   a transmitter;
   wherein gross anatomic siting of said apparatus within said person comprises any of the person's limb, torso, neck, and head; and
   means specifically adapted for surgical fixation of said apparatus within said person at a non-subcutaneous location that comprises any of supramuscular, intramuscular, submuscular, intraluminal, and intracavitary locations.

2. The apparatus of claim 1, further comprising:
   at least one antenna which receives signals that are transmitted to said device and which transmits signals from said device.

3. The apparatus of claim 2, wherein said device or a portion thereof is at least partially shielded to address concerns about exposure of said person to signals generated by, or incidental to, said device.

4. The apparatus of claim 1, wherein said power source may comprises any of a battery, a rechargeable battery, an inductive charging system for charging a battery, and a mechanical or heat sensitive voltage generator.

5. The apparatus of claim 1, wherein implantation of said device is via any of open surgical implantation, laparoscopic implantation, thoracoscopic implantation, endoscopic implantation with or without visualization, direct vision-guided placement.

6. The apparatus of claim 1, wherein said triggering and positioning mechanism continuously polls for a triggering signal after each of a succession of predefined time periods.

7. The apparatus of claim 1, said triggering and positioning mechanism further comprising:
an activation mechanism associated with said device, wherein when an activation event occurs said mechanism receives an action signal from an activation source at said device, and as a result of which said mechanism awakens said device;
wherein when said device is active, it receives positioning data from said positioning source and transmits a positioning signal.

8. The apparatus of claim 7, said activation event comprising any of:
transmission of said action signal from a service provider, emergency services agency by means of any of a cellular telephone or other signaling mechanism, and origination of said action signal by an action of said person.

9. The apparatus of claim 1, said device further comprising:
dynamic software programming for allowing said device to evolve over a specified time, wherein said evolution comprises any of any number of transitions from an active receiver, which sends out a distress signal if said device moves beyond a specified distance from an external signal transmitter, to a passive receiver, which requires a customized signal be sent to said device, at which time said device activates and begins transmitting a distress signal.

10. The apparatus of claim 1, wherein said device is triggered by an external signal, local or remote, placing said device in a pre-configured state.

11. The apparatus of claim 1, wherein said device is a single software phase device which is any of always active, always passive, or somewhere in between.

12. The apparatus of claim 1, wherein aspects of said device's performance which are programmable comprise any of the type of signal to which said device responds, the type of signal said device transmits upon activation, and a permanent shutdown mode.

13. The apparatus of claim 1, wherein dynamic software programming triggers a device stimulation feature which comprises any of a vibration and a shock to said person to alert said person.

14. The apparatus of claim 1, wherein said device continuously sends a notification signal after every predefined time period, wherein a missed signal triggers an alarm.

15. The apparatus of claim 1, further comprising:
means for generating a device activation signal, wherein said activation signal is any of a terrestrial delivered cellular signal, an extra-terrestrially delivered signal, a digital television signal, and a radio-frequency signal.

16. The apparatus of claim 1, further comprising:
means for generating a return/notification signal wherein said return/notification signal is any of a terrestrial, radio-frequency based signal, an extra-terrestrial signal, a cellular based signal, a GSM based signal IDEN, CDMA, IDMA, a GPS based signal, and a scrambling signal having a unique identity which is detected by any of a cable television system and a cellular telephone system.

17. The apparatus of claim 16, wherein said return/notification signal is tracked through any of a series of terrestrial based receiving stations, a series of extra-terrestrial based satellites systems, and a series of mobile receivers.

18. The apparatus of claim 16, wherein said notification signal is a scrambler and is tracked through signal inconsistencies by either of terrestrial based receiving stations and extra-terrestrial based satellites.

19. The apparatus of claim 1, further comprising:
a positioning mechanism comprising any of:
a global positioning system (GPS);
a differential GPS system;
a network assisted GPS (AGPS) system;
an enhanced observed time difference (E-OTD) system;
a network based positioning system;
a cell global identity and timing advance system;
a time difference of arrival system;
an angle of arrival system; and
any combination of the above.

20. The apparatus of claim 19, wherein said positioning mechanism comprises a network assisted GPS (AGPS) system, comprising:
a location server for receiving a GPS snapshot signal from said device;
a fixed reference receiver that receives a GPS signal and that calculates differential corrections that need to be applied to said GPS signal sent from a device user terminal to a location server, wherein said corrections, along with an accurate time signal, are continuously, cyclically, or periodically sent to said location server;
wherein said location sewer receives said corrections from said fixed reference receiver and said GPS snapshot from said device, calculates device location therefrom, and for provides device location information to a tracking service.

21. The apparatus of claim 20, wherein said implantable device comprises an integrated GPS receiver.

22. The apparatus of claim 19, wherein said positioning mechanism comprises an enhanced observed time difference system, comprising:
a mechanism associated with said device for measure control signals from a plurality of surrounding base transceiver stations (BTS);
a mechanism associated with said device for measuring an observed time difference (OTD) between pairs of incoming control signals;
a mechanism associated with said device for putting said measured OTD into a message and for sending said measured OTD to a mobile location center (MLC);
wherein when said MLC receives said message, it contacts a relevant location measurement unit (LMU) and requests OTDs of control signals from all BTSs monitored by said LMU;
wherein using a difference in OTDs of said LMU and said device, said MLC calculates a physical location of said device.

23. A locating and tracking apparatus, comprising:
a positioning and locating device having a unique device identification, wherein said device reposes in a dormant or semi-dormant state, wherein said device comprises an implantable device:
wherein when said device is active, it receives data or signals related to positioning from said positioning source and transmits a signal to be used for positioning;

wherein gross anatomic siting of said device within said person comprises any of the person's limb, torso, neck, and head; and means specifically adapted for surgical fixation of said device within said person at a non-subcutaneous location that comprises any of supramuscular, intramuscular, submuscular, intraluminal, and intracavitary locations.

24. The apparatus of claim 23, wherein said device is activated periodically to take a series of fixes on a person's location.

25. The apparatus of claim 23, said device further comprising:
any of various sensors for monitoring any of a person's body functions, acoustic information, and ambient information.

26. The apparatus of claim 23, wherein said device is configurable to operate in any of several bands and in accordance with any of several protocols to allow continuous locating and tracking a person who is moving through a plurality of geographic areas where different frequency bands and/or protocols are used for communication.

27. The apparatus of claim 23, wherein said device is field programmable for any of: allowing different frequencies or protocols to be activated; allowing a change of said device's unique identity; and interrogating said device for monitored and/or stored information.

28. The apparatus of claim 27, wherein said monitored and/or stored information comprises ambient information.

29. The apparatus of claim 23 further comprising:
an activation mechanism comprising a physical element proximate to, but separate from said device.

30. The apparatus of claim 29, wherein said activation mechanism comprises:
an item proximate to said user, wherein activation signal is generated by any of user activation and loss of proximity to said mechanism.

31. The apparatus of claim 23, further comprising:
at least one additional device; and
means for establishing communication between said devices.

32. An apparatus for locating and tracking a person, comprising:
a human implantable locating and tracking device composed of biocompatible materials in all areas where contact with organic tissue occurs;
wherein gross anatomic siting of said device within said person comprises any of the person's limb, torso, neck, and head; and
means specifically adapted for surgical fixation of said device within said person at a non-subcutaneous location that comprises any of supramuscular, intramuscular, submuscular, intraluminal, and intracavitary locations.

33. An apparatus for locating and tracking a person relative to a positioning source, comprising:
a positioning and locating device implanted within said person and composed of biocompatible materials in all areas where contact with organic tissue occurs,
wherein said device reposes in a dormant or semi-dormant state within said person;
an activation mechanism associated with said device, wherein when an activation event occurs, said mechanism receives an action signal at said device from a remote activation source, and as a result of which said mechanism triggers said device;
wherein when said device is active, it transmits a signal to be used for positioning; and
wherein gross anatomic siting of said device within said person comprises any of the person's limb, torso, neck, and head; and
means specifically adapted for surgical fixation of said device within said person at a non-subcutaneous location that comprises any of supramuscular, intramuscular, submuscular, intraluminal, and intracavitary locations.

34. The apparatus of claim 33, said activation source further comprising:
means for generating an action signal and for transmitting said action signal to said activation mechanism associated with said device.

35. The apparatus of claim 33, further comprising:
a system provider that, upon receipt of said positioning signal from said device, initiates a contact sequence by which appropriate authorities are contacted.

36. An implantable communication apparatus comprising:
a signalling device having a unique identification by which said device triggered from a dormant or semi-dormant state; and
an activation mechanism associated with said device, wherein when an activation event occurs said mechanism receives an action signal at said device;
wherein when said device is active it sends signals representative or local events to a remote location;
wherein said device comprises an implantable device, wherein gross anatomic siting of said device is within a person and comprises any of the person's limb, torso, neck, and head; and
means specifically adapted for surgical fixation of said device within said person at a non-subcutaneous location that comprises any of supramuscular, intramuscular, submuscular, intraluminal, and intracavitary locations.

37. A method for locating and tracking a person, comprising the steps of:
providing a human implantable locating and tracking device composed of biocompatible materials in all areas where contact with organic tissue occurs;
establishing gross anatomic siting of said device within said person at any of the person's limb, torso, neck, and head; and
surgically fixing said device within said person at a non-subcutaneous location that comprises any of supramusoular, intramuscular, submuscular, intraluminal, and intracavitary locations.

* * * * *

UNITED STATES PATENT AND TRADEMARK OFFICE
CERTIFICATE OF CORRECTION

| | | |
|---|---|---|
| PATENT NO. | : 7,102,508 B2 | |
| APPLICATION NO. | : 10/651635 | |
| DATED | : September 5, 2006 | |
| INVENTOR(S) | : Peter Seth Edelstein and Benjamin Theodore Nordell, II | |

It is certified that error appears in the above-identified patent and that said Letters Patent is hereby corrected as shown below:

Claim 4 at column 16, lines 62 and 63, "The apparatus of Claim 1, wherein said power source may comprises" should read --The apparatus of Claim 1, wherein said power source comprises--

Claim 5 at column 17, lines 2 and 3, "with or without visualization, direct vision-guided placement." should read --with or without visualization, and direct vision-guided placement.--

Claim 20 at column 18, lines 35 and 36, "calculates device location therefrom, and for provides" should read --calculates device location therefrom, and provides--

Claim 22 at column 18, lines 43 and 44, "a mechanism associated with said device for measure control signals" should read --a mechanism associated with said device for measuring control signals--

Claim 24 at column 19, lines 9 and 10, "wherein said device is activated periodically to take a series of fixes" should read --wherein said device is activated to periodically take a series of fixes--

Claim 30 at column 19, line 35, "wherein activation signal" should read --wherein an activation signal--

UNITED STATES PATENT AND TRADEMARK OFFICE
CERTIFICATE OF CORRECTION

PATENT NO. : 7,102,508 B2
APPLICATION NO. : 10/651635
DATED : September 5, 2006
INVENTOR(S) : Peter Seth Edelstein and Benjamin Theodore Nordell, II It is certified that error appears in the above-identified patent and that said Letters Patent is hereby corrected as shown below:

Claim 36 at column 20, lines 28 and 29, "a signalling device having a unique identification by which said device triggered" should read --a signaling device having a unique identification by which said device is triggered--; and line 35, "representative or local events" should read --representative of local events--

Signed and Sealed this

Sixth Day of January, 2009

JON W. DUDAS
*Director of the United States Patent and Trademark Office*